US008518341B2

(12) United States Patent
Friderich et al.

(10) Patent No.: US 8,518,341 B2
(45) Date of Patent: Aug. 27, 2013

(54) COLLAPSIBLE STERILIZATION CONTAINER

(75) Inventors: Steven Scott Friderich, Roswell, GA (US); Denise E. O'Connor, Potts Point (AU); Joseph A. Cesa, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/542,908

(22) Filed: Jul. 6, 2012

(65) Prior Publication Data
US 2012/0325706 A1  Dec. 27, 2012

Related U.S. Application Data

(62) Division of application No. 12/317,658, filed on Dec. 24, 2008, now Pat. No. 8,241,587.

(51) Int. Cl.
*A61L 2/00* (2006.01)
*A61L 9/00* (2006.01)
*B65D 83/10* (2006.01)

(52) U.S. Cl.
USPC .......................................... 422/300; 206/363

(58) Field of Classification Search
USPC .......................................... 422/300; 206/363
See application file for complete search history.

(56) References Cited

U.S. PATENT DOCUMENTS

| 2,990,948 | A | 7/1961 | Zackheim |
|---|---|---|---|
| 3,338,992 | A | 8/1967 | Kinney |
| 3,341,394 | A | 9/1967 | Kinney |
| 3,478,868 | A | 11/1969 | Nerenberg et al. |
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,770,119 | A | 11/1973 | Hultberg et al. |
| 3,802,817 | A | 4/1974 | Matsuki et al. |
| 3,849,241 | A | 11/1974 | Butin et al. |
| 3,946,871 | A | 3/1976 | Sturm |
| 3,946,872 | A | 3/1976 | Sturm |
| 3,954,174 | A | 5/1976 | Kraus |
| 4,022,324 | A | 5/1977 | Schuster |
| 4,041,203 | A | 8/1977 | Brock et al. |

(Continued)

FOREIGN PATENT DOCUMENTS

| EP | 0 307 173 A1 | 3/1989 |
|---|---|---|
| EP | 1 762 503 A1 | 3/2007 |
| JP | 2001-286538 A | 10/2001 |
| WO | WO 2007/066359 A1 | 6/2007 |

OTHER PUBLICATIONS

American Society for Testing Materials (ASTM) Designation: E 96-80, "Standard Test Methods for Water Vapor Transmission of Materials," pp. 742-751, published Feb. 1981.
Machine translation of JP 2001-286538 A.

*Primary Examiner* — Walter D Griffin
*Assistant Examiner* — Christopher Vandeusen
(74) *Attorney, Agent, or Firm* — James B Robinson

(57) ABSTRACT

A collapsible single-use sterilization container for use in the sterilization of medical instruments is provided. The sterilization container includes a lid having central portion defined by a frangible region. Upon activation of the frangible region, the central portion may be removed rendering the sterilization container inoperable for future use.

7 Claims, 3 Drawing Sheets

(56) References Cited

U.S. PATENT DOCUMENTS

| | | |
|---|---|---|
| 4,042,109 A | 8/1977 | Barcan |
| 4,049,121 A | 9/1977 | White |
| 4,124,141 A | 11/1978 | Armentrout et al. |
| 4,340,563 A | 7/1982 | Appel et al. |
| 4,417,658 A | 11/1983 | Gardner et al. |
| 4,466,552 A | 8/1984 | Butterworth et al. |
| 4,509,196 A | 4/1985 | Sak et al. |
| 4,553,669 A | 11/1985 | Butterworth et al. |
| 4,644,586 A | 2/1987 | Padgett |
| 4,660,721 A | 4/1987 | Mykleby |
| 4,661,326 A | 4/1987 | Schainholz |
| 4,671,943 A | 6/1987 | Wahlquist |
| 4,706,839 A | 11/1987 | Spence |
| 4,728,504 A | 3/1988 | Nichols |
| 4,766,029 A | 8/1988 | Brock et al. |
| 4,783,321 A | 11/1988 | Spence |
| 4,858,821 A | 8/1989 | Bickelhaupt |
| 4,884,694 A | 12/1989 | Sengewald |
| 4,903,837 A | 2/1990 | Duello |
| 4,915,913 A | 4/1990 | Williams et al. |
| 4,919,888 A | 4/1990 | Spence |
| 4,927,073 A | 5/1990 | Esposito |
| 5,069,355 A | 12/1991 | Matuszak |
| 5,169,706 A | 12/1992 | Collier, IV et al. |
| 5,342,673 A | 8/1994 | Bowman et al. |
| 5,382,400 A | 1/1995 | Pike et al. |
| 5,392,917 A | 2/1995 | Alpern et al. |
| 5,464,688 A | 11/1995 | Timmons et al. |
| 5,520,975 A | 5/1996 | Inoue et al. |
| 5,688,394 A | 11/1997 | McBride, Jr. et al. |
| 5,736,043 A | 4/1998 | Nichols et al. |
| 5,823,340 A | 10/1998 | Maihofer |
| 5,830,547 A | 11/1998 | MacKenzie et al. |
| 6,080,456 A | 6/2000 | Fonteyne |
| 6,162,395 A | 12/2000 | Kowanko |
| 6,217,835 B1 | 4/2001 | Riley et al. |
| 6,312,645 B1 | 11/2001 | Lin et al. |
| 6,312,646 B2 | 11/2001 | Kowanko |
| 6,319,481 B1 | 11/2001 | Banks |
| 6,379,616 B1 | 4/2002 | Sheiman |
| 6,439,625 B1 | 8/2002 | Schainholz et al. |
| 6,468,482 B1 | 10/2002 | Frieze et al. |
| 6,561,352 B2 * | 5/2003 | Sherman et al. ............... 206/366 |
| 6,629,602 B1 | 10/2003 | Heyman |
| 6,889,839 B1 * | 5/2005 | Rosten et al. .................. 206/583 |
| 7,066,329 B2 | 6/2006 | Riley |
| 7,100,768 B2 | 9/2006 | Grimard et al. |
| 7,300,637 B2 | 11/2007 | Lin et al. |
| 7,350,688 B2 | 4/2008 | Sierra-Gomez et al. |
| 7,942,264 B2 | 5/2011 | Friderich et al. |
| 8,241,587 B2 | 8/2012 | Friderich et al. |
| 2002/0098139 A1 | 7/2002 | Sparks |
| 2003/0118491 A1 | 6/2003 | Frieze et al. |
| 2003/0143136 A1 | 7/2003 | Regan |
| 2003/0183547 A1 | 10/2003 | Heyman |
| 2005/0194387 A1 | 9/2005 | Banks |
| 2005/0238530 A1 | 10/2005 | Frieze et al. |
| 2005/0268573 A1 | 12/2005 | Yan |
| 2006/0179793 A1 | 8/2006 | Yewdall et al. |
| 2007/0092398 A1 | 4/2007 | McDonald |
| 2007/0095699 A1 | 5/2007 | Frieze et al. |
| 2008/0000899 A1 * | 1/2008 | Baker et al. .................. 220/4.27 |
| 2010/0158751 A1 | 6/2010 | Friderich et al. |

* cited by examiner

COLLAPSIBLE STERILIZATION CONTAINER

The present application is a Divisional of U.S. patent application Ser. No. 12/317,658 filed on Dec. 24, 2008 now U.S. Pat. No. 8,241,587, in the names of Steven Scott Friderich, Denise E. O'Connor, and Joseph A. Cesa, and claims priority thereto.

BACKGROUND

Sterilization of items used in medical procedures is vital to minimizing the spread of harmful and infectious agents to patients. Typically, the items used in medical procedures are placed into a sterilization container such as sterilization wrap made of a gas permeable material or a reusable vented rigid containers. These sterilization containers preserve sterility of the items contained therein, as well as the interior portion of these containers, after the containers and contents of the container have been channeled through a sterilization procedure. During a typical sterilization procedure, the sterilization wraps or vented rigid containers are placed into a sterilization chamber, and the gas permeable material in the sterilization wrap or vents within the rigid container allow a gas sterilant to contact the item to be sterilized in the sterilization container.

Examples of current gas sterilization procedures include, gas plasma sterilization, steam sterilization, ethylene oxide sterilization, hydrogen peroxide sterilization, and ozone sterilization. Other sterilization procedures, such as irradiation have also been used.

Although utilization of sterilization wrap and/or use of vented rigid re-usable containers are generally effective, there are certain economic and protection disadvantages associated with use of these types of sterilization containers.

For example, with regard to the use of sterilization wraps, the wraps are made of a relatively thin, inexpensive, flexible material. In certain circumstances, prior to wrapping the items with sterilization wrap, the items to be sterilized are placed within a metal sterilization tray having pointed edges. Sometimes, very small tears may develop in the wrap if the wrap snags when it comes into contact with the pointed edge. This may allow bacteria or other harmful substances to contaminate the items therein after the sterilization container is complete. Further, this results in added expense because the items to be sterilized will need to re-handled and re-sterilized at an additional cost.

An additional issue with the use of sterilization wraps is a lack of visibility. Because sterilization wraps generally are not made of transparent material, the medical professional utilizing it cannot visually inspect the items contained therein for content or for assurance that the sterilization procedure has been completed. This can lead to a medical professional opening the wrong sterilization tray during a procedure and/or lead to lack of confidence that the tray is truly sterilized. As a result, trays and articles may require unnecessary rehandling and resterilization which wastes both economic and time resources.

With regard to reusable vented rigid containers, although generally effective, these containers must be thoroughly maintained and cleaned between uses so that they may be re-used. In contrast, sterilization wrap may be discarded after a single use. This re-use of the sterilization container drains an exorbitant amount of hospital economic and time resources because staffing levels often need to be increased in order to maintain these rigid containers. Additionally, the longer the containers are in use, the less confidence clinicians have in the sterilization efficacy of the containers. Ultimately, these containers must be repaired, reconditioned, or discarded.

Thus, there remains a need in the art for sterilization containers that are economical, provide ease of visual inspection, and that impart confidence in sterility among clinicians.

SUMMARY

The present invention provides for single use substantially transparent rigid sterilization containers. The sterilization container includes a tray having a plurality of sides, a base and a rim. The tray may be formed of a substantially transparent material adapted to withstand exposure to steam and ethylene oxide sterilization without degradation of the tray. The plurality of sides of the tray may also include a living hinge. That is, the plurality of sides of the tray may form a seam or seams located at an intersection of adjacent sides of the tray. An additional seam or seams may be fully contained within one side of the tray. Advantageously, the living hinge allows the sides of the trays to be folded down on top of the base to create a low volume storage profile. The sterilization container also includes a lid having a top side, a bottom side, a peripheral portion, and a central portion. The peripheral portion of the lid, which is adapted to fixedly engage the rim of the tray, includes a locking mechanism that engages the rim. The central portion of the lid includes at least one opening therein. The central portion is further defined by a frangible region comprising a plurality of frangible elements and includes a means for removal of the central portion by activation of the frangible region. The sterilization container also includes a gas permeable filter positioned in communication with a side of the lid.

Desirably, the container may be made of a plastic. This allows the contents of the container to be at least partially visible after sterilization of the container and prior to removal of the lid. Additionally, desirably the filter of the container is in communication with the bottom side of the lid but may be in communication with the top side of the lid and may cover the at least one opening in the central portion. Having the filter in communication with the at least one opening allows the sterilant to pass through the filter during the sterilization process in order to contact the items to be sterilized. The filter may be a spunbond, meltblown, spunbond laminate (SMS) but may include may be many other materials which would allow sterilant to pass through it during the sterilization process.

Additionally, the tray may be made of four sides and the central portion of the lid may include frangible elements such scores, perforations, embossments, seams, or combinations thereof. These frangible elements may be activated by applying pressure on the frangible elements and removing the central portion with a hook, handle, tab, or the like.

The locking mechanism may include a cantilevered projection. The locking mechanism may also include sealing polymer engaged with the peripheral portion of the lid. In use, this sealing polymer will melt during the sterilization process and will harden after the process is over. This reinforces and strengthens the seal between the peripheral portion of the lid and tray. The sealing polymer is desirably a polyolefin and desirably has a melting point less than the temperature required for sterilization, desirably less than 134 degrees centigrade.

Another aspect of the invention addresses a single-use container for use in sterilization of medical instrument. The sterilization container includes a top and a bottom composed of a rigid material. The container also includes a plurality of sides made from a non-rigid material and that are attached to the top and the bottom. Desirably, at least one of the four sides includes a peripheral portion defined by a frangible region having a plurality of frangible elements. The peripheral portion may further include a means for removal of the peripheral portion by activation of the frangible region.

Another aspect of the invention addresses methods for sterilizing items for use in a medical procedure. This method includes providing a sterilization container having a tray having a plurality of sides, a base and a rim. The tray may be formed of a substantially transparent material adapted to withstand exposure to steam and ethylene oxide sterilization without degradation of the tray. The sterilization container also includes a lid having a top side, a bottom side, a peripheral portion, and a central portion. The peripheral portion of the lid, which is adapted to fixedly engage the rim of the tray, includes a locking mechanism that engages the rim. The central portion of the lid includes at least one opening therein. The central portion is further defined by a frangible region comprising a plurality of frangible elements and includes a means for removal of the central portion by activation of the frangible region. The sterilization container also includes a gas permeable filter positioned in communication with a side of the lid. The method also includes placing medical instruments inside the sterilization container; inserting the sterilization container into a sterilization chamber for a length of time sufficient to sterilize the medical instruments; and removing the sterilization container from said sterilization chamber. The method may further include the step of providing instructions regarding accessing the sterilized items by removing the central portion with the means for removal of the central portion by activation of the frangible region.

Yet another aspect of the invention addresses methods for sterilizing items for use in a medical procedure. This method includes providing a sterilization container having a top and bottom composed of a rigid material. The container also includes a plurality of sides, composed of a non-rigid material, and attached to the top and the bottom. At least one of the four sides includes a peripheral portion by a frangible region which includes a plurality of frangible elements. Desirably, the peripheral portion further includes a means for removal of the peripheral portion by activation of the frangible region. The method also includes placing medical instruments inside the sterilization container; inserting the sterilization container into a sterilization chamber for a length of time sufficient to sterilize the medical instruments; and removing the sterilization container from the sterilization chamber.

DETAILED DESCRIPTION

The apparatus of the present invention provides for non-reusable rigid sterilization containers for use in medical instrument sterilization procedures. These sterilization containers provide for ease of visual inspection and impart an increased confidence in sterility among clinicians.

The invention will be described with reference to the following description and figures which illustrate certain embodiments. It will be apparent to those skilled in the art that these embodiments do not represent the full scope of the invention which is broadly applicable in the form of variations and equivalents as may be embraced by the claims appended hereto. Furthermore, features described or illustrated as part of one embodiment may be used with another embodiment to yield still a further embodiment. It is intended that the scope of the claims extend to all such variations and embodiments.

Figure 1:
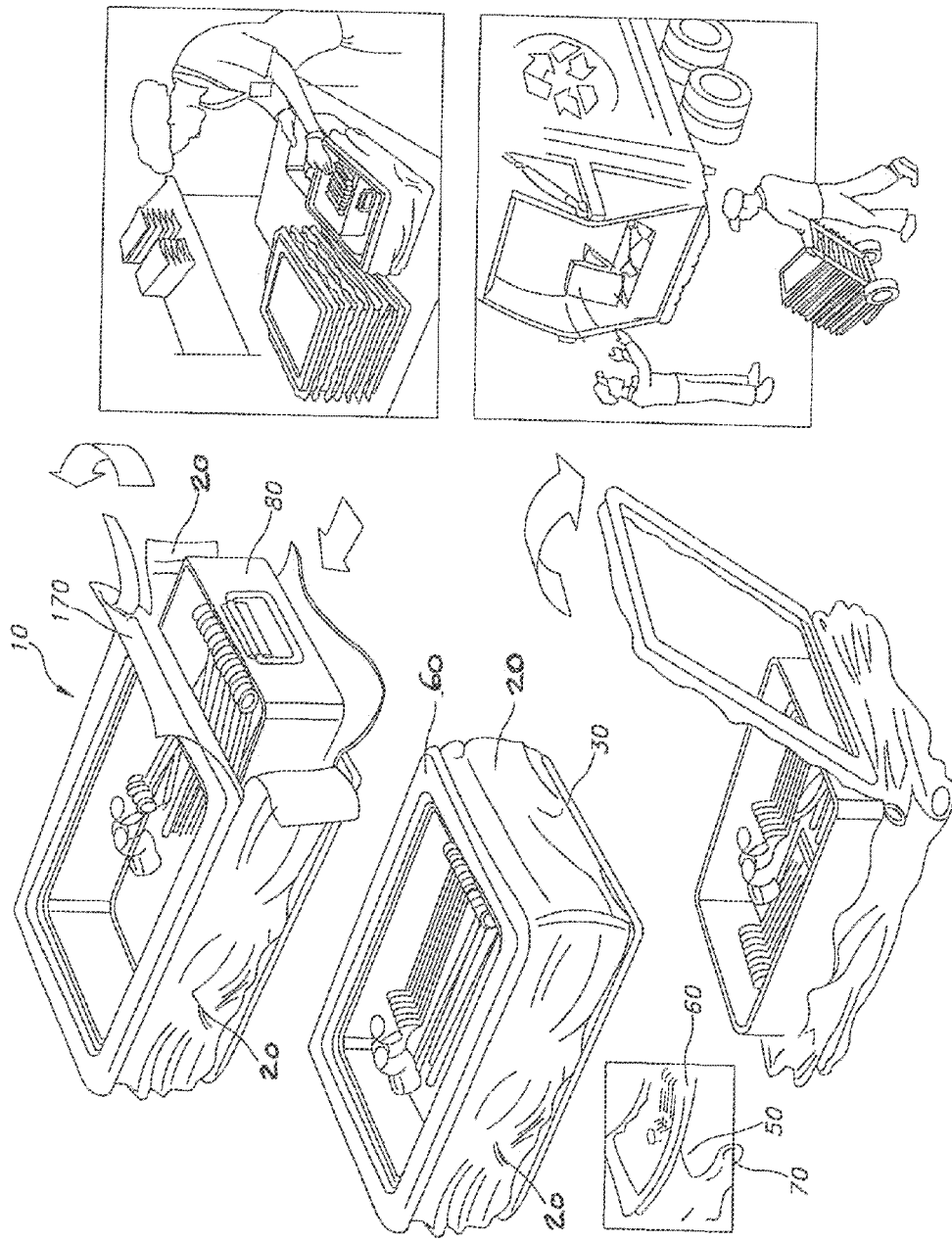
FIG. 1 is a perspective view of a single use sterilization container which includes a rigid top and bottom and non-rigid sides.
Figure 2:
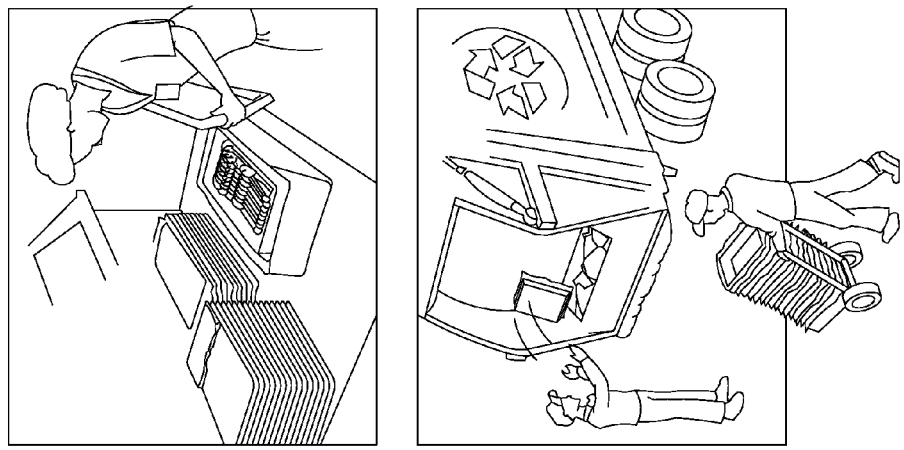
FIG. 2 is a perspective view of a single use sterilization container which includes a filter in communication with the central portion of the lid.
Figure 2:
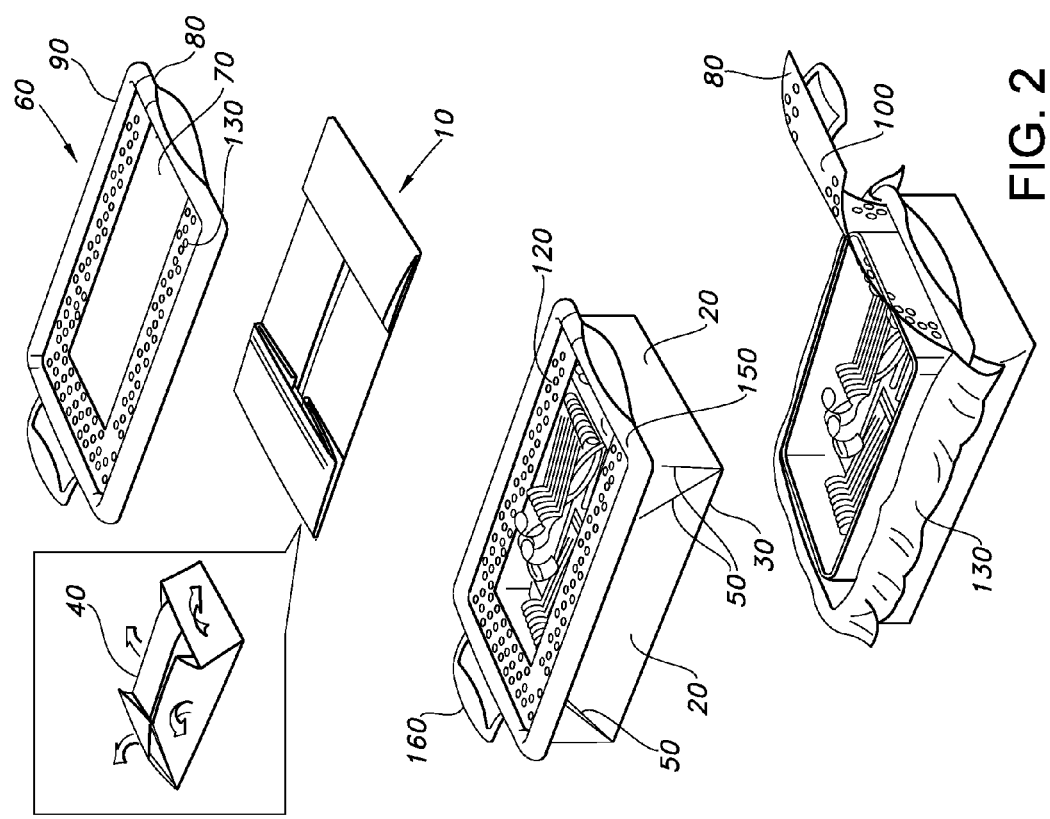

Turning to FIG. 2, a single use sterilization container is provided. The sterilization container includes a tray 10. The tray may be made of a rigid material that is substantially transparent. That is, the tray may be made of a material that allows a viewer of the tray to visualize the contents of the tray by utilizing normal human visual acuity without opening the tray. Further, the rigid material of tray should allow the tray to withstand the temperature required for sterilization of the tray without degradation of the tray. That is, the tray should be able to withstand temperatures of from about 100 degrees centigrade to 300 degrees centigrade without melting, bending, or losing strength. Suitable materials for use in the tray include, but are not limited to, various plastics including polyethylenes and polypropylenes.

The tray may be a variety of shapes and sizes including, but not limited to, circular, oblong, trapezoidal, triangular, rectangular, and square. Additionally, the tray includes a base 30 a rim 40 and may comprises a plurality of sides 20. Advantageously, the tray may also include a living hinge. That is, the plurality of sides of the tray may form a seam 50 or seams located at an intersection of adjacent sides of the tray. An additional seam or seams may be fully contained within one side of the tray.

Regardless of the shape, size, or number of sides, the tray should be adapted to receive a lid 60 in communication with it. Like the tray, the lid may also be composed of a rigid material that may or may not be transparent, such as, for example, various plastics including polypropylene and polyethylene.

Regardless of the type of material that makes up the lid, the lid should include a top side 70, bottom side 80, central portion 100 and peripheral portion 90. In practice, medical instruments for use during a sterilization procedure are placed inside the tray 10. Typical gas sterilization procedures include, for example, gas plasma sterilization, steam sterilization, ethylene oxide sterilization, hydrogen peroxide sterilization, and ozone sterilization.

Once the instruments are placed with the tray, the lid is then snapped onto the tray prior to entering a sterilization chamber. Desirably the lid will include one or more locking mechanisms that allow the peripheral portion of the lid to fixedly engage the rim of the tray. That is, the peripheral portion locks together with the tray and cannot be removed without sufficient force necessary to destroy either a portion of the locking mechanism, the rim, the lid, or combinations thereof so that the tray cannot be easily reconditioned repaired or reused.

Figure 3:
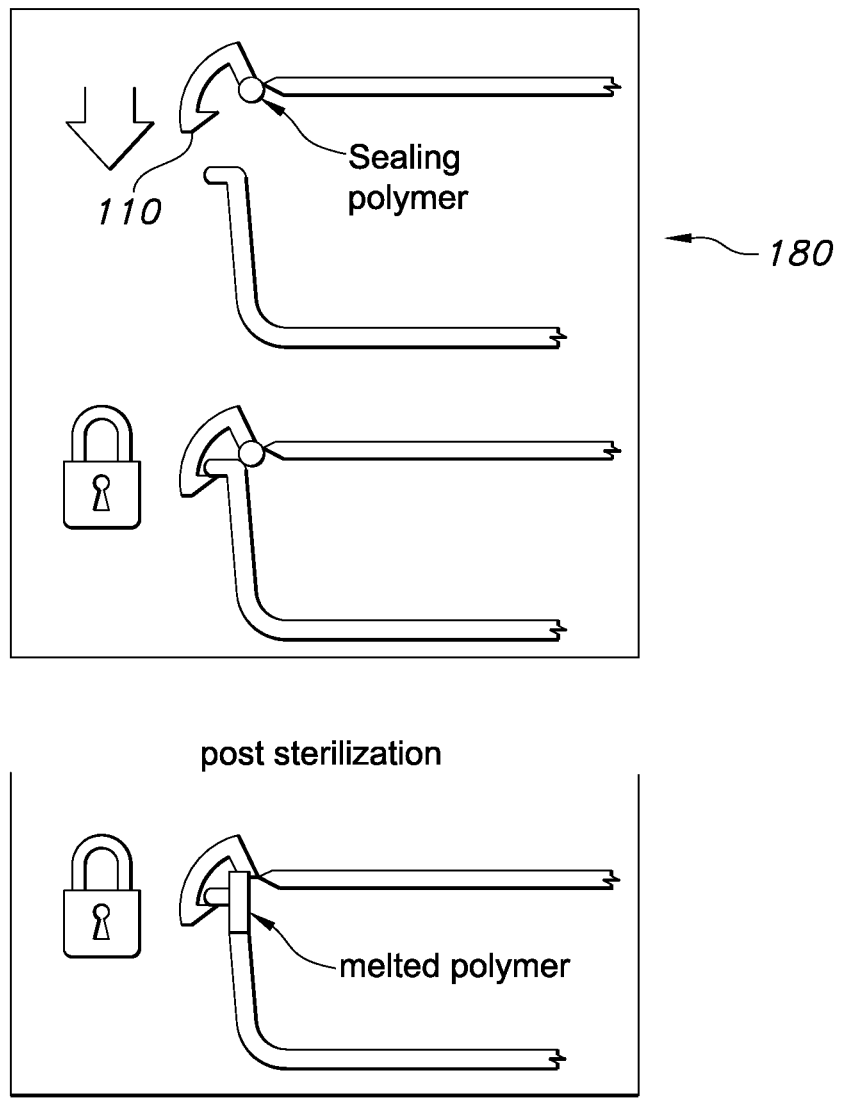
FIG. 3 is a perspective view of locking mechanisms for the single use sterilization container which includes a filter in communication with the central portion of the lid

Turning to FIG. 3, suitable locking mechanisms include, but are not limited to projections that extend from the peripheral portion of the lid and that fixedly engage the rim of the tray. These projections include, but are not limited to, cantilevered projections 110. Additional locking mechanisms may include the use of a sealing polymer 180, such as, for example a sealing polymer made of a polyolfefin. In practice this sealing polymer will melt during the sterilization process and will harden after the process is over. This reinforces and strengthens the seal between the peripheral portion of the lid and tray. Typical sterilization process temperatures range from 100 degrees centigrade to 300 degrees centigrade.

Returning to FIG. 2, the central portion of the lid may also include at least one opening 120 therein and filter 130 which is at least in partial communication with the at least one opening, either on the bottom side or top side of the lid. The opening(s) and filter allow the sterilant to pass through the outside of the sterilization container into the inside of the sterilization container where the medical instruments may be contacted with the sterilant during the sterilization process. Advantageously, upon removal of the central portion of the lid, the filter 130 may be unfolded outward to cover the non-sterile sides and edges of the sterilization container. This allows the clinician to safely and confidently remove the medical instruments from the sterilization container without compromising the sterility of the instruments.

Virtually any gas permeable material may be used in conjunction with or as alternative to a filter provided that the material is permeable to a sterilizing gas but impermeable to airborne microbes, bacteria, viruses and mixtures thereof. Suitable gas permeable materials useable in the present invention include, for example, medical grade paper, nonwoven materials and other similar gas permeable materials. Generally, gas permeable materials which may be used in the present invention are permeable to water vapor and have a minimum water vapor transmission rate (WVTR) of about 300 g/m$^2$/24 hours, calculated in accordance with ASTM Standard E96-80. Suitable medical grade paper includes, for example, AMCOR PLP reinforced coated paper available from AMCOR, Limited.

Suitable nonwoven materials useable as the gas permeable material of the sterilization container of the present invention include, for example, airlaid nonwoven webs, spunbond nonwoven webs, meltblown nonwoven webs, bonded-carded-webs, hydroentangled nonwoven webs, spunlace webs and the like. The method of manufacturing each of these materials is known in the art. Laminates of these materials may also be used.

Of these nonwoven materials, the fibrous material web may comprise a nonwoven meltblown web. Meltblown fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Generally speaking, meltblown fibers may be microfibers that may be continuous or discontinuous, and are generally smaller than 10 microns in diameter, and are generally tacky when deposited onto a collecting surface.

The nonwoven material web may be a nonwoven spunbond web. Spunbonded fibers are small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al. Spunbond fibers are generally not tacky when they are deposited onto a collecting surface. Spunbond fibers can sometimes have diameters less than about 40 microns, and are often between about 5 to about 20 microns.

The nonwoven material web may also comprise a laminate material such as a spunbond/meltblown/spunbond, or SMS, material. A typical SMS material is described in U.S. Pat. No. 4,041,203 to Brock et al. Other SMS products and processes are described, for example, in U.S. Pat. No. 5,464,688 to Timmons et al.; U.S. Pat. No. 5,169,706 to Collier et al.; and U.S. Pat. No. 4,766,029 to Brock et al. Generally, an SMS material will consist of a meltblown web sandwiched between two exterior spunbond webs. Such SMS laminates are available commercially from Kimberly-Clark Corporation under marks such as KIMGUARD®. The spunbonded layers on the SMS laminates provide durability and the internal meltblown layer provides porosity.

As discussed above, once the sterilization containers of the present invention containing the items to be sterilized are placed within the sterilization chamber, the sterilization chamber is closed and a gas sterilant is introduced into the container. The amount of time the items in the compartment are subjected to the gas sterilant depends on various factors, including the type of gas sterilant used, the number of medical instruments placed in the sterilization container as well as other factors. Those skilled in the art will be able to determine the appropriate amount of time the gas sterilant should remain in the chamber based on these and other factors.

Once sterilized, the sterilization containers are removed from the chamber and the sterilization container with the sterilized items contained therein are stored or placed for use. After use, the medical instruments are cleaned and the sterilization containers may be stacked and disposed of or recycled.

Advantageously, the central portion of the lid is defined by a frangible region having a plurality of frangible elements 150. These frangible elements may include, but are not limited to scores, perforations, embossments, seams or combinations thereof as known in the art. These frangible elements create a weaker, less sturdy region within the lid of the container which is adapted to tear or rupture upon application of sufficient force. That is, the frangible region should rupture with the use of ordinary force applied to it by a medical or hospital worker.

Additionally, the central portion may include a means for removal 160 of the central portion. The means for removal may be a hook, handle, tab, body parts, or the like. The frangible region may be activated by applying force or pressure to the frangible elements by use of the means for removal. That is, the frangible region should rupture with the use of ordinary force applied to it by a medical or hospital worker, i.e. one hand applying force to the means for removal. Advantageously the force required for removal of the central portion is concentrated near the means for removal. This lowers the force required for removal. After activation of the frangible region, the central portion of the lid is permanently removed. Thus, after sterilization, and upon removal of the central portion from the lid, the central portion cannot be rejoined with the lid to create a closed sterilization container, and the sterilization container cannot be reused. This is a safety feature designed to prevent the accidental use of non-sterile medical instruments.

Of note, although the frangible region should be flexible enough to allow ease of removal of the central portion, it should be sturdy enough for sterilization containers to be stored, stacked, and/or handled without rupturing the frangible region. Additionally, the filter 130 should overlap the frangible region so that bacteria or other harmful material does not pass through the frangible elements into the inside of the sterilization container after a sterilization procedure has been completed.

In addition to the sterilization container described above, the present invention encompasses a single-use container 10 for use in sterilization of medical instrument. The sterilization container includes a lid or top 20 and a bottom 30 composed of a rigid material that is substantially transparent. That is, the top and bottom may be made of a material that allows a viewer of the top and bottom to visualize the contents located there between by utilizing normal human visual acuity. Further, the rigid material of the top and bottom should allow the top and bottom to withstand the temperature required for sterilization without degradation of the top and bottom. That is, the top and bottom should be able to withstand temperatures of from about 100 degrees centigrade to 300 degrees centigrade without melting, bending, or losing strength. Suitable materials for use in the top and bottom include, but are not limited to, various plastics including polyethylenes and polypropylenes. Further, the top and bottom may be a variety of shapes and sizes including, but not limited to, circular, oblong, trapezoidal, triangular, rectangular, and square.

The container also includes a plurality of sides 20 made from a non-rigid material and that are attached to the top and the bottom. The plurality of sides may be attached to the top and bottom by any method known in the art, including, by way of non-limiting example an adhesive. As discussed above, the non-rigid material may include virtually any gas permeable material such as, for example, a non-woven material. Advantageously, the use of a non-rigid material for the sides allows the sides of the container to be collapsed after use to create a low volume storage profile.

Desirably, at least one of the plurality of sides includes a closable opening for insertion of a medical instruments tray 80 therethrough. Once the tray has been inserted, the side may be closed using any method known the art for closing an opening of a non-rigid material including, for example, applying an adhesive 170 or using a heat seal as known in the art. Thereafter, the sterilization container may be used in a sterilization process as described above.

Desirably, at least one of the four sides includes a peripheral portion 50 defined by a frangible region having a plurality of frangible elements. These frangible elements may include, but are not limited to scores, perforations, embossments, seams or combinations thereof as known in the art. These frangible elements create a weaker, less sturdy region within at least one side of the container which is adapted to tear or rupture upon application of sufficient force. That is, the frangible region should rupture with the use of ordinary force applied to it by a medical or hospital worker.

The peripheral portion may further include a means for removal of the peripheral portion by activation of the frangible region 70. The means for removal may be a hook, handle, tab, body parts, or the like. The frangible region may be activated by applying force or pressure to the frangible elements by use of the means for removal. That is, the frangible region should rupture with the use of ordinary force applied to it by a medical or hospital worker, i.e. one hand applying force to the means for removal. Advantageously the force required for removal of the peripheral portion is concentrated near the means for removal. This lowers the force required for removal. After activation of the frangible region, at least a portion of the peripheral portion is permanently removed and the container can no longer be fully closed. Thus, after sterilization, and upon removal of the peripheral portion from, a gap is left within at least one side and the sterilization container cannot be reused. This is a safety feature designed to prevent the accidental use of non-sterile medical instruments.

In addition to the sterilization containers described above, the present invention encompasses a method for sterilizing items for use in a medical procedure. This method includes providing a sterilization container having a tray having a plurality of sides, a base and a rim. The tray may be formed of a substantially transparent material adapted to withstand exposure to steam and ethylene oxide sterilization without degradation of the tray. The sterilization container also includes a lid having a top side, a bottom side, a peripheral portion, and a central portion. The peripheral portion of the lid, which is adapted to fixedly engage the rim of the tray, includes a locking mechanism that engages the rim. The central portion of the lid includes at least one opening therein. The central portion is further defined by a frangible region comprising a plurality of frangible elements and includes a means for removal of the central portion by activation of the frangible region. The sterilization container also includes a gas permeable filter positioned in communication with a side of the lid. The method also includes placing medical instruments inside the sterilization container; inserting the sterilization container into a sterilization chamber for a length of time sufficient to sterilize the medical instruments; and removing the sterilization container from said sterilization chamber. The method may further include the step of providing instructions regarding accessing the sterilized items by removing the central portion with the means for removal of the central portion by activation of the frangible region.

In addition to the sterilization containers described above, the present invention encompasses yet another method for sterilizing items for use in a medical procedure. This method includes providing a sterilization container having a top and bottom composed of a rigid material. The container also includes a plurality of sides, composed of a non-rigid material, and attached to the top and the bottom. At least one of the four sides includes a peripheral portion by a frangible region which includes a plurality of frangible elements. Desirably, the peripheral portion further includes a means for removal of the peripheral portion by activation of the frangible region. The method also includes placing medical instruments inside the sterilization container; inserting the sterilization container into a sterilization chamber for a length of time sufficient to sterilize the medical instruments; and removing the sterilization container from the sterilization chamber.

We claim:

1. A single-use container for use in sterilization of medical instruments, the container comprising:
    a top comprised of a rigid material;
    a bottom comprised of a rigid material;
    a plurality of sides attached to the top and the bottom and comprised of a non-rigid material that allows the sides of the container to be collapsed after use, wherein at least one of said sides is comprised of a gas permeable material, wherein at least one of the sides comprises a peripheral portion defined by a frangible region comprising a plurality of frangible elements, the peripheral portion further comprising a means for removal of the peripheral portion by activation of the frangible region.

2. The container of claim 1 wherein the top and the bottom comprise a plastic.

3. The container of claim 1 wherein the plurality of frangible elements are scores, perforations, embossments, seams or combinations thereof.

4. The container of claim 1 wherein the means for removal of the peripheral portion is a hook, handle or a tab.

5. The container of claim 1, wherein each of the sides comprises a spunbond, meltblown, spunbond (SMS) laminate.

6. The container of claim 1 wherein the container has four sides and said four sides are attached to the top and the bottom.

7. The container of claim 1 wherein at least one of the plurality of sides comprises a closable opening for insertion of a medical instruments tray therethrough.

* * * * *